(12) United States Patent
Roy et al.

(10) Patent No.: US 8,779,110 B2
(45) Date of Patent: Jul. 15, 2014

(54) PURIFICATION OF LOW ISOELECTRIC POINT ISOFORMS OF DARBEPOIETIN

(75) Inventors: Chaiti Roy, Hyderabad (IN); Darshan Koticha, Hyderabad (IN); Vivek Arthanari, Hyderabad (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 541 days.

(21) Appl. No.: 12/997,292

(22) PCT Filed: Jun. 23, 2009

(86) PCT No.: PCT/US2009/048239
§ 371 (c)(1),
(2), (4) Date: Dec. 10, 2010

(87) PCT Pub. No.: WO2010/008823
PCT Pub. Date: Jan. 21, 2010

(65) Prior Publication Data
US 2011/0098452 A1    Apr. 28, 2011

(30) Foreign Application Priority Data
Jun. 24, 2008    (IN) .......................... 1536/CHE/2008

(51) Int. Cl.
*A23J 1/00*    (2006.01)
*C07K 1/00*    (2006.01)

(52) U.S. Cl.
USPC ............ 530/413; 530/415; 530/416; 530/417

(58) Field of Classification Search
None
See application file for complete search history.

(56) References Cited

U.S. PATENT DOCUMENTS

2006/0246544 A1 * 11/2006 Kang et al. .................... 435/69.1
2007/0275882 A1 * 11/2007 Meijer et al. ...................... 514/8

FOREIGN PATENT DOCUMENTS

| WO | 00/27869 A1 | 5/2000 | |
|---|---|---|---|
| WO | 03/045996 A1 | 6/2003 | |
| WO | 2006/126066 A2 | 11/2006 | |
| WO | WO 2013/058485 * | 4/2013 | ............... C07K 1/22 |

OTHER PUBLICATIONS www.princeton.edu/~achaney/tmve/wiki100k/docs/Isoelectric_point.html, downloaded Aug. 1, 2013.*
Collins 1997. Separation and Purification Methods 26:215-253.*
J.C. Egrie et al., "Development and Characterization of Novel Erythropoiesis Stimulating Protein (NESP)," British Journal of Cancer, vol. 84 (Supplement), pp. 3-10, 2001.
Kevin G. Rice et al., "Quantitative Mapping of the N-Linked Sialyloligosaccharides of recombinant Erythropoietin: Combination of Direct High-Performance Anion-Exchange Chromatography and 2-Aminopyridine Derivatization," Analytical Biochemistry, vol. 206, Issue 2, pp. 278-827, 1992—Abstract.
Anna Caldini et al., "Epoetin Alpha, Epoetin Beta an Darbepoetin Alfa: Two-Dimensional Gel Electrophoresis Isoforms Characterization and Mass Spectrometry Analysis," Proteomics, vol. 3, pp. 937-941, 2003.
Francoise Lasne et al., "Detection of Isoelectric Profiles of Erythropoietin in Urine: Differentiation of Natural and Administered Recombinant Hormones," Analytical Biochemistry, vol. 311, pp. 119-126, 2002.
Joris R. Delanghe et al., "Testing for Recombinant Erythropoietin," American Journal of Hematology, vol. 83, pp. 237-241, epub Oct. 4, 2007—Abstract.
H. Sasaki et al., "Carbohydrate Structure of Erythropoietin Expressed in Chinese Hamster Ovary Cells by a Human Erythropoietin cDNA ," Journal of Biological Chemistry, Vo. 262, pp. 12059-12076, 1987.
R. S. Rush et al., "Microheterogeneity of Erythropoietin Carbohydrate Structure," Analytical Chemistry, vol. 67, pp. 1442-1452, 1995.
R. S. Rush et al., "Peptide Mapping and Evaluation of Glycopeptide Microheterogeneity Derived from Endoproteinase Digestion of Erythropoietin by Affinity High-Performance Capillary Electrophoresis," Analytical Chemistry, vol. 65, pp. 1834-1842, 1993.
J. C. Egrie et al., "The Role of Carbohydrate on the Biological Activity of Erythropoietin," Glycoconj. Journal, vol. 10, pp. 263, 1993.
S. Elliot et al., Blood, vol. 96, pp. 8 2a, 2000.
Gokana et al., Journal of Chromatography, vol. 701, pp. 109-118, 1997.

* cited by examiner

*Primary Examiner* — Shulamith H Shafer
(74) *Attorney, Agent, or Firm* — Pergament Gilman & Cepeda LLP; Milagros A. Cepeda; Edward D. Pergament

(57) ABSTRACT

The invention provides an efficient method of purification of a modified cytokine. The process includes the use of a chromatographic technique for the purification of the desired cytokine. The purified cytokine can be used as a therapeutic composition.

30 Claims, 2 Drawing Sheets

PURIFICATION OF LOW ISOELECTRIC POINT ISOFORMS OF DARBEPOIETIN

INTRODUCTION

Aspects of the present invention relate to processes for separation of low pI isoforms of darbepoetin from a mixture of isoforms.

Erythropoietin or EPO is a glycosylated cytokine that is produced by the liver and kidney cells and regulates red blood cell production. Purified recombinant human EPO can be administered to human patients for the treatment of medical problems associated with inadequate red blood cell supply, e.g., anemia and chronic renal failure.

The polypeptide backbone of the human EPO molecule has an invariant amino acid sequence; however, the carbohydrate side chains exhibit microheterogeneity in sugar content and structure (Sasaki H, et al., *J. Biol. Chem.*, 1987; 262:12059-76, Rush R S, et al., *Anal. Chem.*, 1995; 67:1442-52 and Rush R S, et al., *Anal. Chem.*, 1993; 65:1834-42) A negatively charged sialic acid molecule typically caps the end of each arm of a carbohydrate chain. As a consequence, the variable nature of the carbohydrate chains in general and sialic acid content in particular gives rise to EPO isoforms with differences in charge (Rush R S, et al., *Anal. Chem.*, 1995; 67:1442-52). Egrie and coworkers (Egrie J C., and Browne J K., *Br. J. Cancer*, 2001; 84, 3-10 and Egrie et al., *Glycoconj. J.*, 1993; 10:263-269) discovered a direct correlation between the number of sialic acid groups on the carbohydrate part of rHuEPO and both its serum half-life and biological activity. Erythropoietin isoforms with more sialic acid residues exert greater biological activity as sialic acid residues prevent the fast clearance in vivo.

Darbepoetin is a novel erythropoiesis stimulating protein or an EPO analog with five N-linked carbohydrate chains and up to 22 sialic acids. In contrast, recombinant human EPO has three N-linked carbohydrate chains and a maximum of 14 sialic acids (Egrie J C., and Browne J K., *Br. J. Cancer*, 2001; 84, 3-10 and Elliot S, et al, *Blood*, 2000; 96:8 2a). As a result of the additional glycosylation, darbepoetin exhibits a three-fold longer serum half-life and increased in vivo activity with respect to recombinant human EPO. Darbepoetin isoforms arise mainly due to their variant glycosyl content with variant numbers of negatively charged terminal sialic acid residues. Isoforms with higher sialic acid content have a low pI. These low pI isoforms of darbepoetin have proved to be of higher therapeutic value, for example the product sold as ARANESP® by Amgen Corporation.

The literature discloses purification of EPO and its analogs by anion exchange chromatography, alone or in combination with hydrophobic interaction or size exclusion chromatographic techniques.

International Application Publication No. WO 00/27869 discloses a process for purification of erythropoietin consisting of a sequence of hydrophobic interaction, anion exchange, cation exchange and size exclusion chromatographic steps. International Application Publication No. WO 03/045996 discloses chromatographic purification of recombinant human erythropoietin by reverse phase chromatography, anion exchange and size exclusion chromatography. Gokana et. al, *Journal of Chromatography*, Vol. 701, 1997, pages 109-118 describe a method of chromatographic separation of recombinant human erythropoietin isoforms by DEAE-Sephacel chromatography.

Thus, the disclosures have a complex series of chromatographic steps for the purification of erythropoietin and its analogs. However, an efficient and simple process is desired to separate the low pI isoforms of darbepoetin from a mixture of isoforms.

SUMMARY

Aspects of the present invention provide processes for the isolation of isoforms of darbepoetin. In embodiments, the processes are used for the isolation of low pI isoforms of darbepoetin. In particular embodiments, the processes are used for the isolation of isoforms of pI of about 4.5 or less.

Isolation or purification of isoforms is done using at least one cation exchange chromatographic step in the flow-through mode. The processes use a range of pH and salt concentration to separate the low pI isoforms from mixtures of darbepoetin isoforms.

In an aspect, the invention provides processes for the isolation of low pI isoforms of darbepoetin from a mixture of darbepoetin isoforms, said process comprising at least one cation exchange chromatography step in the flow-through mode.

In an aspect, the invention provides processes for the isolation of low pI isoforms of darbepoetin from a mixture of darbepoetin isoforms, said process comprising at least one cation exchange chromatography step in the flow-through mode and further at least one anion exchange chromatography step.

In an aspect, the invention provides processes for the isolation of low pI isoforms of darbepoetin from a mixture of darbepoetin isoforms, said process comprising at least one cation exchange chromatography step in the flow-through mode and further at least one mixed mode exchange chromatography step.

DETAILED DESCRIPTION

Figure 1:
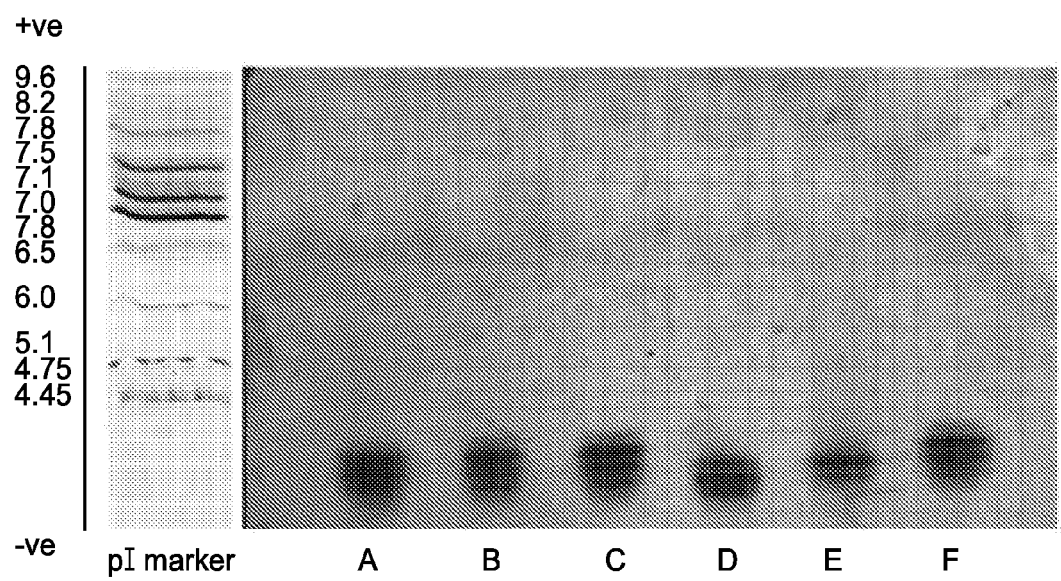
FIG. 1 is an isoelectric focusing gel obtained in the experiment of Example 6, showing the low pI isoforms obtained in the eluate of Q sepharose step described in Example 5.

Aspects of the present invention relate to processes for the isolation of low pI isoforms of darbepoetin by cation exchange chromatography in the flow-through mode.

The present invention includes methods wherein the low pI isoforms are separated from a mixture of isoforms comprising at least one cation exchange chromatographic step in the flow-through mode. This simultaneously acts as the viral inactivation step due to the low pH range buffer used in the step to obtain the desired isoforms.

The term "isoforms," as used herein, refers to proteins with identical amino acid sequence but differing with respect to charge and therefore isoelectric point, as a result of differences in glycosylation, acylation, deamidation or sulfation.

The "isoelectric point" or "pI" is the pH at which a particular molecule or surface carries no net electrical charge. The "pI" of a polypeptide refers to the pH at which the polypeptide's positive charge balances its negative charge. The pI can be estimated using various known methods, e.g., from the net charge of the amino acid and/or sialic acid residues on the polypeptide or by using isoelectric focusing, chromatofocusing, etc.

Low pI isoforms are isoforms having pI of about 4.5 or less.

In one embodiment the low pI isoforms are isolated by a process comprising an anion exchange chromatographic step or mixed mode chromatographic step that includes at least one cation exchange chromatographic step in the flow-through mode.

In another embodiment the low pI isoforms are isolated from a mixture of isoforms by a process comprising the steps of an anion exchange or mixed mode chromatographic step, and a cation exchange chromatographic step in the flow-through mode, which could optionally be followed by another anion exchange or mixed mode chromatographic step.

In yet another embodiment the low pI isoforms are isolated from a mixture of isoforms by a process which comprises the steps of an anion exchange or mixed mode chromatographic step, a first cation exchange chromatographic step in the flow-through mode, and a second cation exchange chromatographic step in the flow-through mode.

In yet another embodiment the low pI isoforms are separated or purified from a mixture of other isoforms by a process that comprises anion exchange or mixed-mode chromatography, a first cation exchange chromatography in the flow-through mode, and a second cation exchange chromatography in the flow-through mode, followed by another anion exchange or mixed mode chromatographic step.

In yet another embodiment the low pI isoforms are separated or purified from a mixture of other isoforms by a process comprising the steps of an anion exchange chromatography, a first cation exchange chromatography in the flow-through mode, and a second cation exchange chromatography in the flow-through mode, followed by a mixed mode chromatographic step.

The embodiments mentioned herein may optionally comprise any of tangential flow filtration, concentration, diafiltration or ultrafiltration steps, between the chromatographic steps.

The embodiments mentioned here may include one or more viral inactivation steps or sterile filtration or nanofiltration steps.

Anion exchange chromatography mentioned in the embodiments may be carried out using any weak or strong anion exchange chromatographic resin or a membrane which could function as a weak or a strong anion exchanger. An example of anion exchange chromatographic resin or membrane is Q-Sepharose chromatographic resin or membrane.

Cation exchange chromatography mentioned in the embodiments may be carried out using any weak or strong cation exchange chromatographic resin or a membrane which could function as a weak or a strong cation exchanger. An example of a weak cation exchange resin is carboxymethyl-sepharose (CM-sepharose) or a resin with a similar carboxymethyl ligand.

Mixed mode chromatography mentioned in the embodiments refers to chromatographic resins in which more than one chromatographic separation principles, typically ionic and hydrophobic, are operative. Thus a mixed mode resin refers to a solid phase with cationic or anionic, hydrophobic moieties or ligands. The term "solid phase" is used to mean any non-aqueous matrix. Mixed-mode chromatographic ligands show either hydrophobic or charged interactions or both. An example of a mixed mode resin is a Captoadhere resin or any mixed mode resin that functions in a similar way.

"Flow-through mode" in the cation exchange step refers to processes wherein the desired protein is not bound to the column and is obtained in the flow-through solution during loading or post load washing step. The desired protein in the flow-through can be collected as various fractions and pooled together or can be collected as a single fraction.

The buffers used herein for loading the protein in the cation exchange chromatographic step have pH values about 2 to about 5, or 2.8 to about 4.8, or about 3 to about 3.5. The buffers used herein for obtaining the protein during the wash step have pH values about 2 to about 5, or about 2.8 to about 4, or about 3 to about 3.5.

The pH of the buffer used in a first cation exchange step may be different from the pH used in a second cation exchange step.

The buffering agents used for making the buffer solution may comprise sodium acetate or sodium citrate or phosphate buffer, and their salts or derivatives. In embodiments, the buffering agent has a concentration of about 10 mM to about 100 mM, or about 40 to about 90 mM, or about 75 to about 85 mM in concentration.

Certain specific aspects and embodiments of the invention are more fully described by reference to the following examples, being provided only for purposes of illustration. These examples should not be construed as limiting the scope of the invention in any manner.

Example 1

Expression and Harvest of the Protein.

Chinese Hamster Ovary (CHO) production cell lines are made by transduction of the CHO-S parental cell line with retrovector from the Darbepoetin alpha expression vector (pCS-Darbepoetin-WPE (new ori). After transduction, the pooled population of cells are expressing up to 36 µg/ml of Darbepoetin alpha after 10-14 days in T-flasks. The pooled population of cells is diluted to very low cell density (1-3 viable cells/ 200 µl media) and plated in 96 well microtiter plates to establish clonal cell lines that originate from single cells. Clones are screened for darbepoetin alpha production and the clones with high productivity are selected for expression.

The cells expressing darbepoetin alpha are expanded from the master cell bank in 3 stages of spinners and one stage of seed reactor before being inoculated into the production reactor.

PF CHO medium is used for culturing the cells in spinners in order to obtain good cell growth and high viability. The PF-CHO medium contains, per liter of medium: PF-CHO main powder 6.0 g, PF-CHO base powder 10.4 g, L-Glutamine 0.58 g, Pluronic F-68 1.0 g, sodium bicarbonate 2.0 g. The pH of the medium is set at 7 before inoculation. Cells from the master cell bank are inoculated in a spinner bottle containing PF-CHO medium at an initial cell count of 0.2 million cells/mL. The spinner bottles are incubated in a 5% $CO_2$ incubator maintained at 37° C. After 72 hours of incubation when the cell density reaches 1 million cells/mL, cells are harvested and transferred to another stage. After 3 stages of transfer in spinner bottles, cells are inoculated in a 6.5 L seed reactor containing 4 L SFM-6(1) medium at an initial cell density of 0.2 million cells/mL. The SFM-6(1) medium contains, "DMEM/F-12" basal media, amino acids, insulin, vitamins, trace elements, plant peptone, bicarbonate and fructose sugar. In the seed reactor, the pH is maintained at 7.0 and temperature of culture is controlled at 37.0° C. Dissolved oxygen is maintained at 40% by controlling agitation and aeration. After 72 hours when the cell density reaches 1 million cells/mL, culture is aseptically harvested and cells are transferred to a 11 L production reactor containing 10 L of SFM-6(2) medium at an initial cell density of 0.2 million cells/mL. Culture is harvested after 12 days to collect the supernatant containing desired product.

Example 2

Capture by Anion Exchange Chromatography or Captoadhere Chromatography.

After clarification of the crude extract, the clarified cell culture broth is concentrated and the conductivity is reduced by diafiltration (using a tangential flow filtration (TFF) with a molecular weight cut off of 30 kDa) using 25 mM Tris, 60 mM NaCl buffer of pH 7.1. The concentrated cell culture broth is then loaded into the Q-Sepharose column that was pre-equilibrated with 5 column volumes (CV) of 25 mM Tris, 60 mM NaCl, pH 7.1 buffer. The column was then washed with 5 CV of the equilibration buffer (25 mM Tris, 60 mM NaCl, pH 7.1). This was followed by a low pH wash with 80 mM Sodium Acetate, 40-120 mM NaCl buffer of pH 4.0. Another wash with the equilibration buffer was performed. The desired protein loaded on to the column was eluted with 25 mM Tris, 140-300 mM NaCl buffer of pH 7.1.

Alternatively, CaptoAdhere (mixed mode chromatographic column) can be used in place of Q-Sepharose column. The Captoadhere column is pre-equilibrated with 5 CV of 20 mM Phosphate, 60 mM NaCl, pH 7.1±0.2 buffer. The column is then washed with 5 CV of the equilibration buffer (20 mM Phosphate, 60 mM NaCl, pH 7.1±0.2). This is followed by a low pH wash with 80 mM Sodium Acetate, 40-120 mM NaCl buffer of pH 4.0. Another wash with the equilibration buffer is performed. The desired protein loaded on to the column is eluted with 20 mM Phosphate, 140-300 mM NaCl buffered at pH 7.1±0.2.

Example 3

First Cation Exchange Chromatography.

Fractions of the eluate from Example 2 are pooled and concentrated and the conductivity is reduced by diafiltration by a TFF step using 73 mM Sodium Acetate buffer of pH 4.8. This step acts as a buffer exchanging step wherein the pooled eluate of Q-Sepharose column is brought into 73 mM sodium acetate buffer of pH 4.8. The buffer exchanged sample is then loaded onto the CM-Sepharose column that has been pre-equilibrated with 5 CV of 73 mM sodium acetate buffer of pH 4.8. The desired product is obtained in the flow-through while loading the sample, while the impurities are bound to the column. After loading, the column is washed with 3 CV of 73 mM sodium acetate buffer of pH 4.8. The desired product is obtained as flow-through in the wash step as well. Impurities bound to the column are subsequently eluted with 25 mM Tris, 500 mM NaCl buffer of pH 7.1.

Example 4

Second Cation Exchange Chromatography.

The flow-through fractions from Example 3, or fractions of the eluate from Example 2, are pooled, concentrated and exchanged with buffer containing 83 mM sodium acetate (or 80-85 mM sodium acetate) pH 3.3 (or pH 3.0-3.5) using TFF. Sample from TFF is loaded onto a CM-Sepharose column pre-equilibrated with 5 CV of 83 mM sodium acetate buffer of pH 3.3. The desired product is obtained in the flow-through while loading the sample. The pH of the buffer used in this step is found essential to get the required isoforms in the flow-through. Also the above process is continued for more than 30 minutes thus simultaneously it acted as a virus inactivation step. After loading, the column is washed with 9 CV of 73 mM sodium acetate buffer of pH 4.8. The desired product is obtained in the flow-through of the wash step as well. Impurities bound to the column are subsequently eluted with 25 mM Tris, 500 mM NaCl buffer of pH 7.1.

Example 5

Anion Exchange Chromatographic Step or CaptoAdhere Chromatographic Step.

The flow-through fractions from Example 4 are loaded onto a Q-Sepharose column that has been pre-equilibrated with buffer containing 25 mM Tris, 60 mM NaCl, pH 7.1. The column is washed with the same buffer. Desired product is bound to the column and is eluted with 40 mM phosphate, 280 mM NaCl buffered at pH 6.0.

Alternatively, CaptoAdhere (a mixed mode chromatographic column) can be used in place of Q-Sepharose column. In this case, the column is pre-equilibrated with 5 CV of 20 mM phosphate buffer of pH 6.0 and washed again with the same buffer (5 CV). Desired protein bound to the column is then eluted with 4 CV of buffer containing 40 mM phosphate and 280 mM NaCl, pH 6.0.

This step (Example 5) acts as a concentration and buffer exchanging step, thus eliminating the need for another TFF. Also this offers a more controlled environment than the normal TFF.

Example 6

Isoelectric Focusing.

The flow through fractions of Example 4 and eluate from Example 5 are analyzed by Isoelectric Focusing (IEF). The IEF gel is prepared using water, urea, 30% acrylamide, and ampholyte (pH range 2-4 and 3-10). The above components are mixed gently and 10% w/v ammonium persulfate and TEMED are added to the mixture and the mixture is cast in a gel sandwich apparatus (BIORAD Mini Protean Cell) and fitted with a comb. The gel is allowed to polymerize for 45 minutes at room temperature. A small amount of protein solution is mixed with an equal volume of sample buffer (glycerol, Ampholyte and Milli Q water) and loaded into the gel. The gel is then placed in a BIORAD Mini Protean Cell assembly and filled with a cathode buffer (25 mM sodium hydroxide) and anode buffer (25 mM orthophosphoric acid) in separate compartments. The flow through fractions from Example 4 or eluate from Example 5 are run at 200 V constant voltage for 1.5 hours for pre-focusing of ampholytes at room temperature and then the voltage is increased to 400 V and run for the next 1.5 hours at room temperature. After the run, the gel is carefully removed and stained using either a coomassie or silver stain, as disclosed in the art.

FIG. 1 shows an isoelectric focusing gel from an experiment performed as described above, showing the low pI isoforms obtained in the eluate of Q sepharose step described in Example 5. Lanes A to F are different purification batches performed in accordance with the invention; that is, harvests of cell cultures expressing darbepoetin alpha are subjected to anion exchange chromatography as described in Example 2, followed by cation exchange chromatography in the flow through mode, as described in Example 4, followed by anion exchange chromatography, as described in Example 5.

Figure 2:
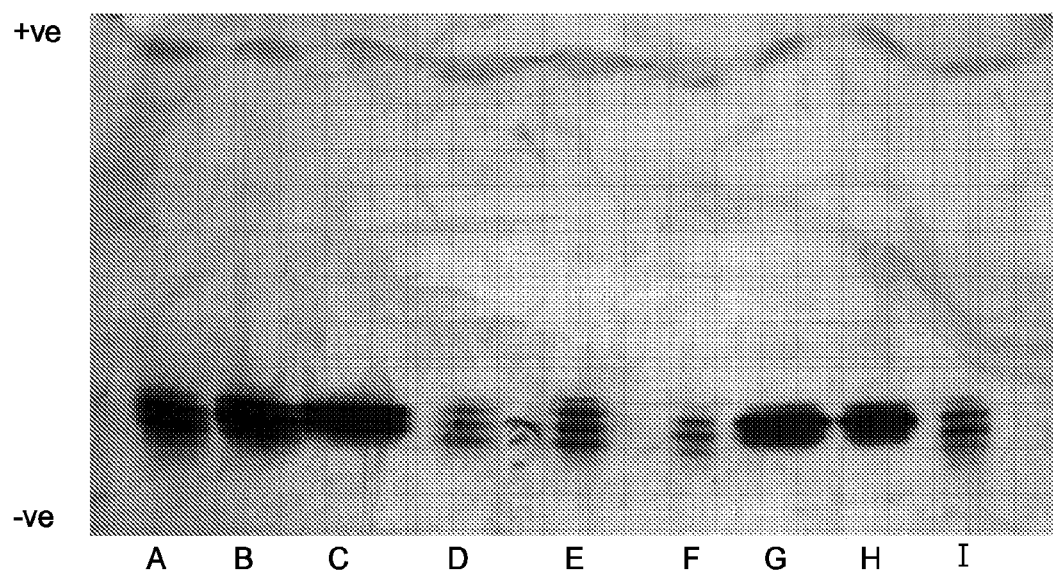
FIG. 2 is an isoelectric focusing gel obtained in the experiment of Example 6, showing the low pI isoforms obtained in the flow-through of the CM-Sepharose step performed as described in Example 4.

FIG. 2 shows an isoelectric focusing gel from an experiment performed as described above, showing the low pI isoforms obtained in the flow-through of the CM-Sepharose step performed as described in Example 4. Lanes A to C and F to I in the figure are different purification batches performed in accordance with the invention; that is, harvests of cell cultures expressing darbepoetin alpha are subjected to anion exchange chromatography as described in Example 2, followed by cation exchange chromatography in the flow through mode, as described in Example 4. Lanes D and E are isoforms observed in commercially available samples of darbepoietin alpha ARANESP® (pI 2.8-3.3) and used as standards for comparison.

The invention claimed is:

1. A process for the isolation of isoforms of darbepoetin of isoelectric point (pI) less than 4.5 from a mixture of darbepoetin isoforms, said process comprising at least one cation exchange chromatography step in the flow-through mode at about pH 3 to about pH 4.8.

2. The process according to claim 1, wherein the said isoforms have pI values less than about 4.5.

3. The process according to claim 1, further comprising at least one anion exchange chromatography step wherein anion exchange chromatography precedes and/or follows at least one cation exchange chromatography.

4. The process according to claim 3, wherein at least one anion exchange chromatography step precedes at least one cation exchange chromatography step.

5. The process according to claim 3, wherein at least one anion exchange chromatography step follows at least one cation exchange chromatography step.

6. The process according to claim 3, wherein at least one anion exchange chromatography step precedes at least one cation exchange chromatography step and at least one anion exchange chromatography step follows at least cation exchange chromatography step.

7. The process according to claim 1, comprising two cation exchange chromatography steps.

8. The process according to claim 7, wherein at least one anion exchange chromatography step precedes at least one cation exchange chromatography step.

9. The process according to claim 7, wherein at least one anion exchange chromatography step follows at least one cation exchange chromatography step.

10. The process according to claim 7, wherein at least one anion exchange chromatography step precedes at least one cation exchange chromatography step and at least one anion exchange chromatography step follows at least one cation exchange chromatography step.

11. The process according to claim 1, further comprising at least one mixed mode chromatography step wherein mixed mode chromatography precedes and/or follows at least one cation exchange chromatography.

12. The process according to claim 11, wherein at least one mixed mode chromatography step precedes at least one cation exchange chromatography step.

13. The process according to claim 11, wherein at least one mixed mode chromatography step follows at least one cation exchange chromatography step.

14. The process according to claim 11, wherein at least one mixed mode chromatography step precedes at least one cation exchange chromatography step and at least mixed mode chromatography step follows at least one cation exchange chromatography step.

15. The process according to claim 11, comprising two cation exchange chromatography steps.

16. The process according to claim 15, wherein at least one mixed mode chromatography step precedes at least one cation exchange chromatography step.

17. The process according to claim 15, wherein at least one mixed mode chromatography step follows at least one cation exchange chromatography step.

18. The process according to claim 15, wherein at least one mixed mode chromatography step precedes at least one cation exchange chromatography step and at least one mixed mode chromatography step follows at least one cation exchange chromatography step.

19. The process according to claim 3, comprising at least one mixed mode chromatography step wherein mixed mode chromatography precedes and/or follows at least one anion cation exchange chromatography.

20. The process according to claim 19, wherein at least one mixed mode chromatography step precedes the cation exchange chromatography step.

21. The process according to claim 19, wherein at least one mixed mode chromatography step follows the cation exchange chromatography step.

22. The process according to claim 19, wherein at least one mixed mode chromatography step precedes at least one cation exchange chromatography step and at least one anion exchange chromatography step follows at least cation exchange chromatography step.

23. The process according to claim 19, wherein at least one anion exchange chromatography step precedes at least one cation exchange chromatography step and at least one mixed mode chromatography step follows at least one cation exchange chromatography step.

24. The process according to claim 19, comprising two cation exchange chromatography steps.

25. The process according to claim 24, wherein the mixed mode chromatography step precedes at least one cation exchange chromatography step.

26. The process according to claim 24, wherein the mixed mode chromatography step follows at least one cation exchange chromatography step.

27. The process according to claim 24, wherein the mixed mode chromatography step precedes at least one cation exchange chromatography step and the anion exchange chromatography step follows at least one cation exchange chromatography step.

28. A The process according to claim 24, wherein the anion exchange chromatography step precedes at least one cation exchange chromatography step and the mixed mode chromatography step follows at least one cation exchange chromatography step.

29. The process according to claim 1, wherein the flow-through is obtained at pH values about 3.3.

30. The process according to claim 29, wherein the flow-through is obtained at a pH about 4.8.

* * * * *